United States Patent
Levine et al.

(10) Patent No.: US 6,824,853 B1
(45) Date of Patent: Nov. 30, 2004

(54) PLIABLE PAD FOR COLLECTING AND ABSORBING LIQUIDS

(75) Inventors: Daniel S. Levine, Wayne, PA (US); David E. Levine, Devon, PA (US); Marshall S. Levine, Wayne, PA (US)

(73) Assignee: Alpha Scientific Corporation, Malvern, PA (US)

( * ) Notice: Subject to any disclaimer, the term of this patent is extended or adjusted under 35 U.S.C. 154(b) by 160 days.

(21) Appl. No.: 09/691,272

(22) Filed: Oct. 18, 2000

(51) Int. Cl.⁷ .................. B32B 3/16; B32B 23/02
(52) U.S. Cl. ................ 428/77; 428/78; 428/190; 428/191; 405/60; 442/378
(58) Field of Search ............... 428/77, 78, 190, 428/191; 405/60; 442/378

(56) References Cited

U.S. PATENT DOCUMENTS

| | | |
|---|---|---|
| 2,815,883 A | 12/1957 | Robins et al. |
| 3,834,527 A | 9/1974 | Howe |
| 3,911,921 A | 10/1975 | Svensson |
| 4,206,570 A | 6/1980 | Cooper |
| 4,765,323 A | 8/1988 | Poettgen |
| 5,060,803 A | 10/1991 | Beer et al. |
| 5,135,792 A | 8/1992 | Hogan |
| 5,161,544 A * | 11/1992 | Morris ............ 128/849 |
| 5,429,633 A | 7/1995 | Davis et al. |
| 5,803,920 A | 9/1998 | Gilman |
| 5,845,769 A | 12/1998 | Yeager |
| 6,199,553 B1 * | 3/2001 | Hafer et al. ......... 128/849 |

* cited by examiner

Primary Examiner—Glenn Caldarola
Assistant Examiner—Alexis Wachtel
(74) Attorney, Agent, or Firm—Gary M. Cohen

(57) ABSTRACT

A pliable pad includes a layer formed of an absorbent material and a formable material arranged generally parallel to each other. The selected formable material, such as aluminum foil, is capable of assuming a desired shape and of retaining the desired shape which has been assumed. As a result, the formable material can be shaped so that the pliable pad defines a basin for collecting and absorbing liquids. The pliable pad can also include one or more layers for defining a liquid barrier. The pliable pad can be used to collect excess liquid produced during a medical procedure, such as the irrigation of a wound, or can be used in other, non-medical applications in which liquid is to be collected.

59 Claims, 16 Drawing Sheets

PLIABLE PAD FOR COLLECTING AND ABSORBING LIQUIDS

BACKGROUND OF THE INVENTION

This invention relates primarily to the fields of wound treatment and surgery, and more particularly, to improvements in the formation of a basin which can be used to collect liquid used in wound irrigation. The present invention can also be used in other fields, including non-medical applications.

Absorbent pads are routinely used in clinics and in homes. Such pads essentially comprise a combination of an absorbent material and a fluid barrier. A mesh is typically provided over the absorbent material to retain the absorbent material against the fluid barrier, which serves as a backing for the pad.

For use in irrigating a wound, known absorbent pads have generally been found to be insufficient because unabsorbed, contaminated liquid frequently spills from the periphery of the pad. The spilled liquid constitutes a safety hazard and a health hazard, and frequently requires corrective action.

SUMMARY OF THE INVENTION

To overcome these and other problems associate with known absorbent pads, the present invention provides a pliable pad which can be shaped into a trough or basin (either before use or in situ) for containing excess liquid. In this way, the pliable pad of the present invention can prevent liquid from spilling from the trough or basin which is formed (e.g., onto the floor or onto medical personnel).

The pliable pad of the present invention can also be used in non-medical applications such as the containment of liquid leaking from a plumbing fixture or from a machine. This can be especially useful in situations in which a simple pan or bucket cannot be deployed because of limited access, or when such devices would provide inadequate containment of a leak or spray. In such cases, the pliable pad can be used to overcome the problems associated with the use of simple pans or buckets by introducing the pliable pad in one configuration (e.g., flat or partially folded) and by then shaping the pliable pad, in place, to address the problems associated with limited access. In addition, the pliable pad can be shaped to surround the leak, to limit or even eliminate any spray that might otherwise escape.

In its most basic configuration, the pliable pad of the present invention is comprised of an absorbent material arranged adjacent to a formable material. The absorbent material and/or the formable material can further include a barrier to liquid, or a separate liquid barrier layer can be provided.

The formable material is preferably chosen so that it can be shaped manually, and so that the desired shape will be retained indefinitely if left undisturbed. The formable material can then be manipulated by hand, to form a wall or a series of walls, so that the pliable pad can form a fluid-collecting basin. As examples, the pliable pad can be made formable by mating the absorbent material with a sheet formed of a metal or a metal foil, or by embedding an elongated bendable member (e.g., a wire, rod or tube) within the absorbent material or within a sheet (or sheets) resting upon the absorbent material or to which the absorbent material is attached.

The resulting structure will then provide an absorbent material located within a basin which is defined by the walls created by manipulating the formable material. Any liquid that is not absorbed by the absorbent material will nevertheless be retained within the basin, providing added assurances that the fluids in question are effectively collected by the resulting structure.

The formable material, or the liquid barrier, can be provided with an extension formed of a liquid-impervious material which can be folded over the pliable pad. The liquid-impervious material can then be draped over the wound to permit convenient irrigation of the wound while protecting the user from contact with hazardous liquid or spray. The liquid-impervious material is preferably, but not necessarily, transparent to further facilitate the procedure to be performed.

A draining conduit or port can also be provided, if desired, to conduct excess liquid to a separate or external receptacle. Alternatively, a portion of the formable material can itself be shaped to create a draining conduit.

The pliable pad of the present invention can further include one or more tabs attached to the pliable pad, one purpose of which is to provide a means for securing the pliable pad to the patient (or to a desired structure). The tabs can either be tied to each other, or fastened together by other means. The tabs can assist in supporting the walls which have been formed in their desired position, and can also provide a means for sealing the pliable pad against a patient (or to a desired structure) so that the likelihood of a leakage of liquid is reduced.

The pliable pad of the present invention will generally include a layer (or section) formed of an absorbent material, which can include a permeable material that allows fluid to pass to the absorbent material without allowing the absorbent material to be released. The layer (or section) of absorbent material and the formable material can be joined together by an adhesive, by heat sealing, or by other means. Alternatively, the layer (or section) of absorbent material can be mechanically attached to the formable material (e.g., by bending over edges of the formable material to capture the layer (or section) of absorbent material) without the use of an adhesive. Another alternative is to simply locate the layer (or section) of absorbent material adjacent to the formable material, without being bonded to the formable material. Yet another alternative is to sandwich the formable material between a pair of sheets, with at least one of the sheets comprising a liquid barrier, if needed. The sheets can be heat welded to each other, or attached with an adhesive, to encase the formable material between the pair of sheets.

The present invention is also directed to various uses for the pliable pad. The primary use for the pliable pad is in irrigating wounds. To this end, the head or a limb of a patient is placed on a pliable pad which is manipulated to form a basin to contain the appendage. The desired irrigation step is then performed. During such irrigation, liquid is capable of being absorbed by the absorbent material, and any liquid that is not absorbed by the absorbent material is collected in the basin defined by the pliable pad.

The pliable pad of the present invention also has uses in fields other than medicine. For example, the pliable pad can be used to collect water leaking from plumbing fixtures, such as sinks, or to collect liquids that drain or leak from machinery. Any of a variety of uses are possible.

For a further description of the pliable pad of the present invention, reference is made to the description of preferred embodiments of the invention which is provided below, together with the following drawings.

DESCRIPTION OF PREFERRED EMBODIMENTS

Figure 1:
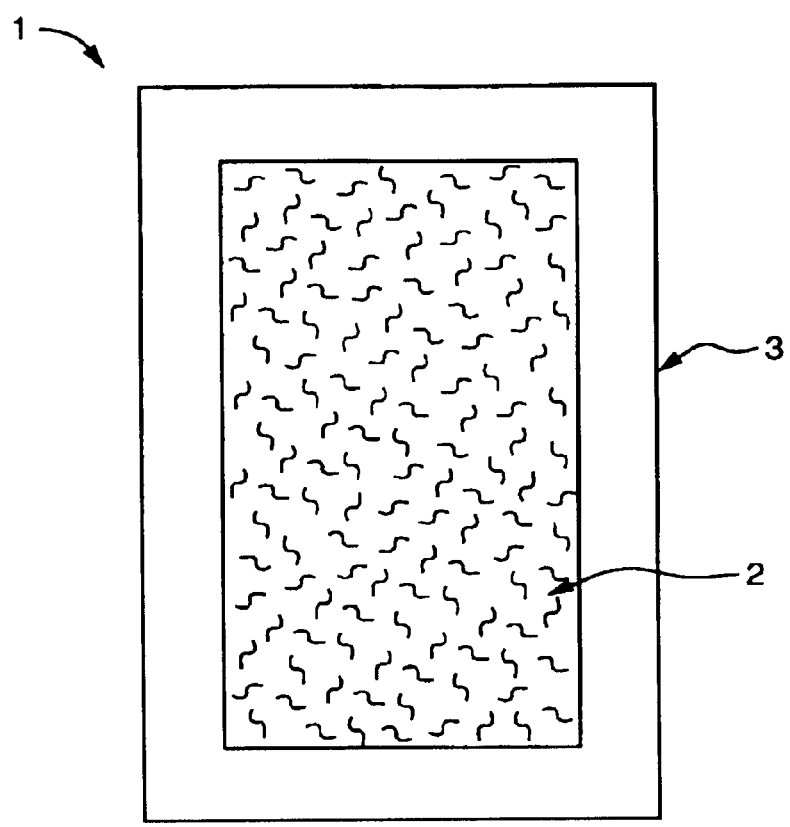
FIG. 1 is a plan view showing an embodiment of the pliable pad of the present invention.

FIG. 1 shows a basic embodiment of the pliable pad of the present invention. As used in this specification, the term "pliable pad" refers to the entire composite structure described below.

The pliable pad 1 generally includes a center section 2 which is combined with a backing layer 3. The center section 2 is comprised of an absorbent material, which can be formed of a superabsorbent polymer, a pulp material or the like, or any other material capable of absorbing liquids. The backing layer 3 preferably forms a liquid barrier, and can be formed of one or a plurality of layers formed of selected liquid-retaining materials (which may be the same or different from one another). Preferred liquid-retaining materials can include any of a variety of plastic sheet materials or plastic coatings, with particularly preferred materials for developing the liquid barrier including plastic films formed of vinyl, polyethylene, polypropylene or some other equivalent plastic.

Either the center section 2 or the backing layer 3, or both, includes a "formable material" which, as used in this specification, will refer to any material which is capable of assuming a desired shape and of retaining the desired shape which has been assumed. Preferred examples of such formable materials include thin sheets of aluminum or aluminum foil, metal wires, rods or bands, or other structurally equivalent materials. The formable material can be provided in a smooth condition, or can be crinkled or dimpled to increase its strength, as desired. Any of a variety of structurally formable materials can be used, provided the selected material is bendable and can retain its shape after being formed into a particular configuration.

The selected formable material can be implemented as a single layer, as plural layers, or as a composite which includes the formable material. A preferred, composite formable material for use in accordance with the present invention is comprised of two layers of foil separated by a plastic film or coating between the foil layers to reduce the likelihood of leaks through any holes which might come to be formed in the foil layers. The formable material is preferably capable of bending in virtually any direction, for formation into an unlimited variety of shapes.

In the embodiment shown in FIG. 1, the area of the backing layer 3 is greater than that of the center section 2. For such a configuration, the center section 2 is preferably comprised of the absorbent material and the backing layer 3 is preferably comprised of the formable material. However, the pliable pad 1 of the present invention is not limited to such an arrangement. For example, in configurations where the center section 2 is substantially coextensive with the backing layer 3, the center section 2 can include the formable material together with the absorbent material. In such cases, when the pad is formed into a basin, the absorbent material will cover the walls of the basin, as well as the bottom.

Figure 2:
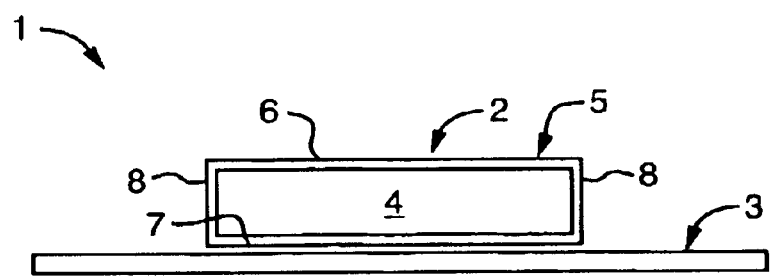
FIG. 2 is a cross-sectional view of an embodiment of the pliable pad of FIG. 1, showing an optional outer layer for surrounding the absorbent material.

FIG. 2 shows a cross-section of the pliable pad 1 shown in FIG. 1. The illustrated cross-section again includes both the center section 2 and the backing layer 3 of FIG. 1. The center section 2 includes a layer 4 formed of the absorbent material, which is surrounded with and enclosed by an outer layer 5 (including top 6, bottom 7 and side 8 portions), encasing the layer of absorbent material 4. The primary purpose of the outer layer 5 is to allow fluid to pass through, to the absorbent material, while preventing particles or fibers of the absorbent material from being released into an open wound. A secondary purpose of the outer layer 5 is to provide a means for reliably locating the layer of absorbent material 4 relative to the backing layer 3, by securing the layer 4 to the layer 3 when deemed appropriate.

For some applications, such as in an operating room, the outer layer 5 may not provide sufficient protection against the release of dust particles from the absorbent material. In such cases, the absorbent material can be formed of a material such as absorbent gauze or superabsorbent fibers, which tend not to release particles. The outer layer 5 can be omitted in such cases, or retained, as preferred.

The outer layer 5 will typically be formed of a mesh, non-woven, or equivalent material capable of allowing fluid to pass through the outer layer 5 and to the layer of absorbent material 4 contained by the outer layer 5. The outer layer 5 will preferably completely encase the layer of absorbent material 4, and either can simply rest on the layer of absorbent material 4 or can be attached to the layer of absorbent material 4 using, for example, an adhesive, heat welds, or another equivalent fastening means. Alternatively, the bottom 7 of the outer layer 5 can be omitted and the sides 8 of the outer layer 5 can be attached to the backing layer 3.

The outer layer 5 can be comprised either entirely of one material, such as a mesh, or can be constructed from a combination of mesh-like and liquid-impervious materials. A particularly preferred embodiment uses a mesh material for the sides 8 and a liquid-impervious material for the top 6, with the bottom 7 either being omitted, made of a liquid-impervious material or made of a mesh material. In this arrangement, the liquid-impervious material positioned along the top 6 of the outer layer 5 serves to keep a body part being treated from resting in a direct fluid path with the absorbent material. Fluid is then allowed to flow over the facing defined by the top 6 of the outer layer 5, and through the mesh forming the sides 8 of the outer layer 5 to the layer of absorbent material 4, in this way limiting the amount of fluid that the appendage contacts directly.

In cases where the outer layer 5 is constructed from a combination of mesh-like and liquid-impervious materials, the outer layer 5 can be implemented either as a single layer, with the liquid-impervious material provided along the top 6 joined at its edges to the mesh layer along one or more of the sides 8 of the outer layer 5, or as plural sections or multiple layers of material. For example, the mesh material can encase the entire layer of absorbent material 4, with sections of liquid-impervious material forming a second layer on top of or beneath the mesh material along the top 6 and/or the bottom 7 of the outer layer 5, so that only the sides 8 (and possibly the bottom 7) allow fluid to reach the layer of absorbent material 4. Alternatively, and as mentioned previously, the outer layer 5 can be eliminated if preferred. It is also possible to provide only a top portion 6 which is formed of the liquid-impervious material, and to omit the bottom 7 and the sides 8 of the outer layer 5, if desired for a particular application.

Figure 3A:
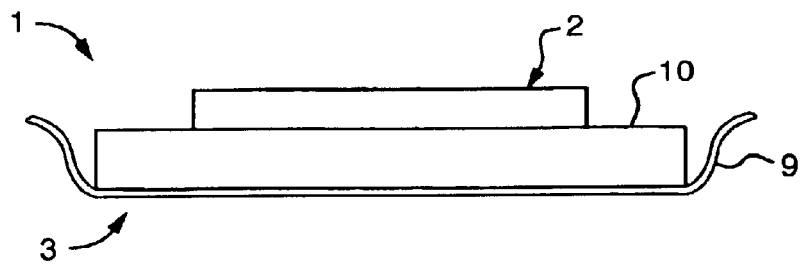
FIGS. 3A to 3D are cross-sectional views illustrating various configurations for accommodating the formable material, which also show optional layers of a liquid-impervious material.
Figure 3B:
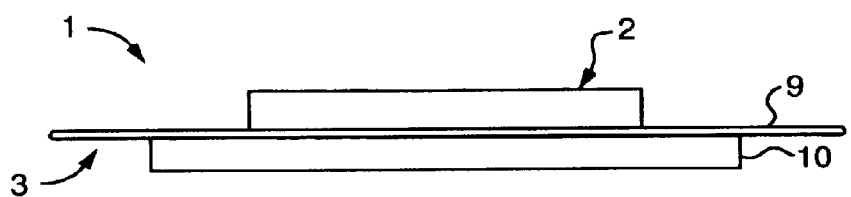

FIGS. 3A to 3D show cross-sectional views of several alternative configurations for a formable backing layer 3 for the pliable pad 1 shown in FIG. 1. In FIG. 3A, a liquid barrier layer 9 and a layer of formable material 10 jointly comprise the formable backing layer 3. In this configuration, the formable material alone generally will not provide a sufficient liquid barrier, and the use of an additional liquid barrier layer 9 is generally preferred in such cases. The liquid barrier layer 9 is typically comprised of a plastic sheet, film or coating, and can be deployed above and/or below the layer of formable material 10, as is shown in FIGS. 3B and 3A, respectively. The arrangement of FIG. 3B would be suitable, for example, in cases where the formable material is implemented as a wire mesh (e.g., using a soft "chicken wire"), which will tend to retain its shape, but which will not serve as a liquid barrier. The liquid barrier layer 9 can be deployed as a single layer, or in multiple layers if preferred.

Figure 3C:
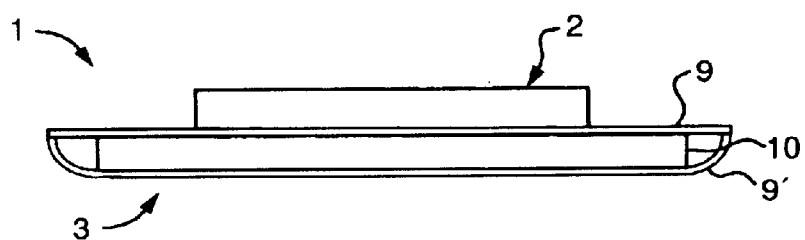
Figure 3D:
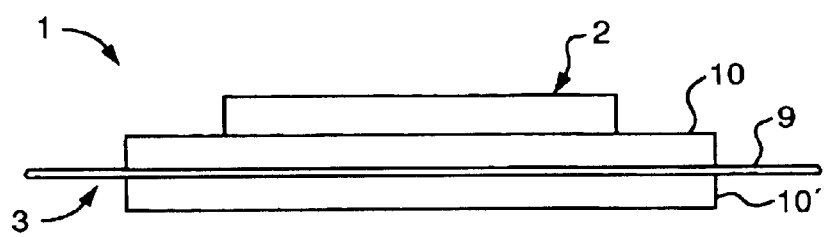

FIG. 3C illustrates an embodiment which employs two layers 9, 9' formed of a liquid barrier material. In this configuration, the liquid barrier layers 9, 9' are used to contain the layer of formable material 10. A liquid barrier layer 9 can also be positioned between multiple layers 10, 10' of the formable material, as is shown in FIG. 3D (which illustrates one of potentially multiple internal liquid barrier layers). Combinations of the foregoing structural configurations can also be developed, if desired.

Figure 4A:
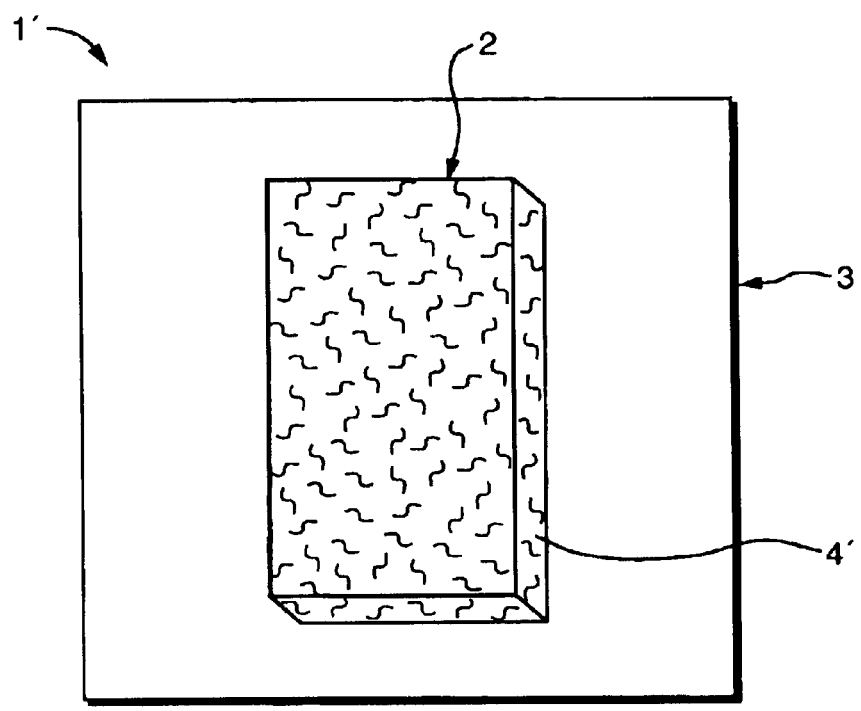
FIG. 4A is an isometric view of an alternative embodiment of the pliable pad which includes a thick absorbent material located at the center of the pad.

FIG. 4A shows an alternative embodiment for the pliable pad (1') which is similar to the pliable pad 1 of FIG. 1, except for the thickness and the surface area of the layer of absorbent material 4'. The thickened layer of absorbent material 4' shown in FIG. 4A is primarily used to support an appendage above the liquid level (i.e., above any contaminated fluid which has collected in the basin) during irrigation. Providing a relatively thick layer of absorbent material 4' also serves to concentrate the absorbent material where most of the liquid will tend to gather.

As examples, the thickness of the layer of absorbent material 4 in the embodiment of FIGS. 1 and 2 can be in the range of from about ⅛ to about ¼ inches, while the thickness of the layer of absorbent material 4' in the embodiment of FIG. 4A can be in the range of from about 1 to about 2 inches. This results in a layer of absorbent material for the embodiment shown in FIG. 4A which can be on the order of as much as 16 times the thickness of the layer of absorbent material for the embodiment shown in FIG. 1. Such thicknesses are presently considered preferred. However, other thicknesses can freely be used if preferred for a given application.

Figure 4B:
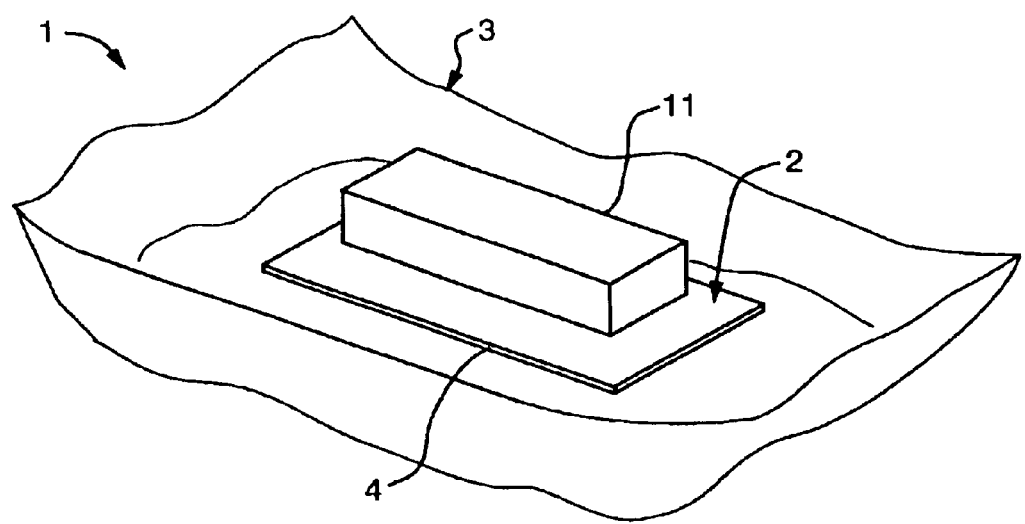
FIGS. 4B and 4C are isometric views of alternative embodiments of the pliable pad which include a support for lifting an article placed on the pliable pad.
Figure 4C:
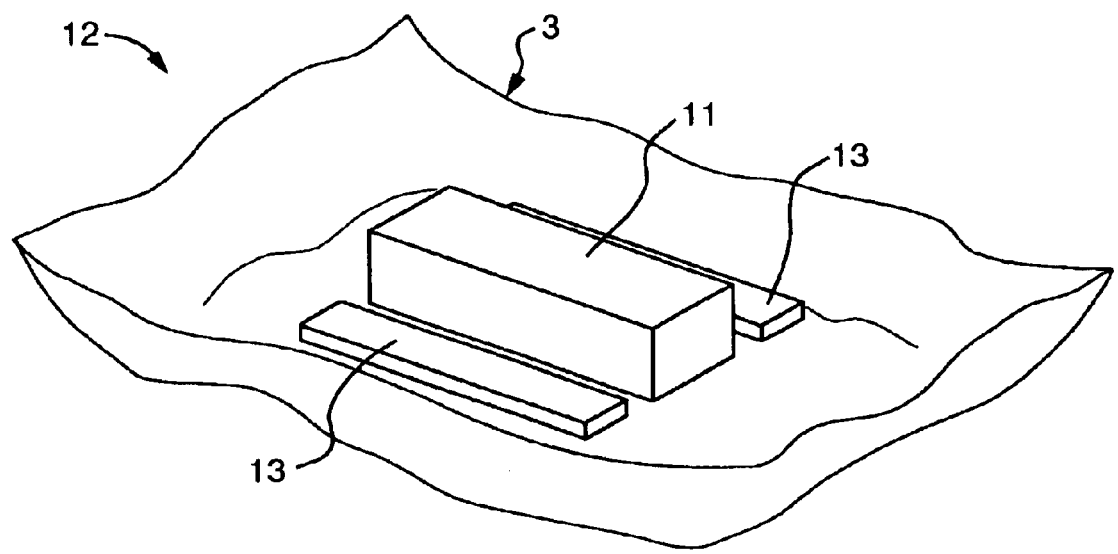
Figure 4D:
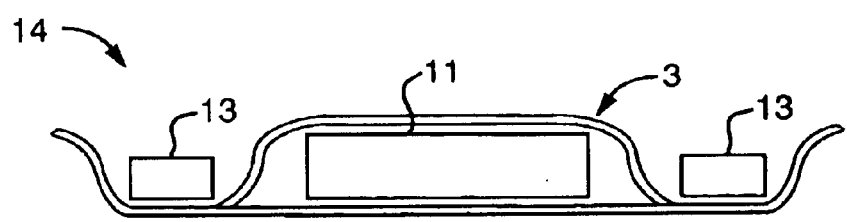
FIG. 4D is a cross-sectional view of an alternative embodiment of the pliable pad which includes a support for lifting an article placed on the pliable pad.

FIGS. 4B to 4D show alternative embodiments for the pliable pad, each having a support 11 which can be used to lift an appendage or other object, primarily for purposes of raising the appendage or the other object above the predominant fluid collecting surfaces of the pliable pad. In FIG. 4B, the support 11 is located on top of the center section 2 (which is formed of the layer of absorbent material 4) of the pliable pad 1. In FIG. 4C, the support 11 is placed directly on top of the backing layer 3 of the pliable pad 12, and a pair of members 13 formed of the absorbent material are positioned on opposite sides of the support 11. Equivalent arrangements, including plural supports 11 and/or plural members 13 formed of the absorbent material placed at various locations on the backing layer 3, are also possible.

A support can also be positioned beneath the layer of absorbent material so that the absorbent material extends beyond the sides of the support, as well as over the top surface of the support. As a further alternative, the support can be positioned beneath the backing layer. For example, FIG. 4D shows an alternative embodiment for the pliable pad (14) which has a support 11 positioned between two layers 9 formed of a liquid barrier material, which combine to develop the backing layer 3 for the pliable pad 14, combined with a pair of members 13 formed of the absorbent material. Again, other arrangements including the support 11, either as part of or beneath the backing layer 3, can also be developed.

Figure 5A:
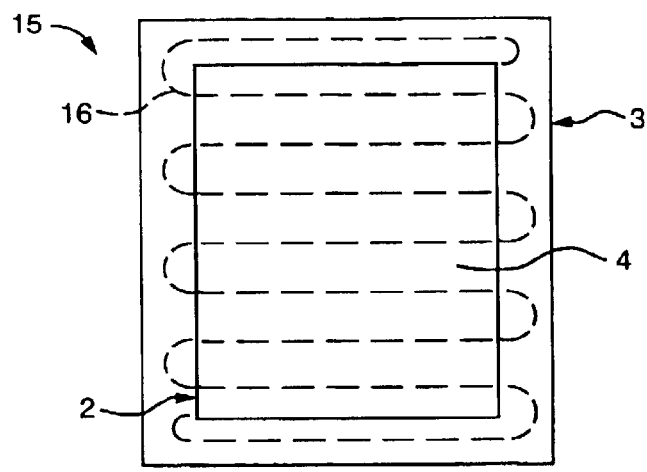
FIGS. 5A and 5B are plan views showing alternative embodiments of the pliable pad having an internal, formable member.

FIG. 5A shows an alternative embodiment for the pliable pad (15) having an elongate bendable member 16 (e.g., a wire, rod or tube) which is combined with the layer of absorbent material 4 to serve as a formable material. In this embodiment, the layer of absorbent material 4 is made formable by the stiffening effect of the member 16 which is mated with the layer of absorbent material 4. Since the layer of absorbent material 4 is not normally also a liquid barrier, the layer of absorbent material can also be combined with one or more separate layers formed of a liquid barrier material, if desired.

Figure 5B:
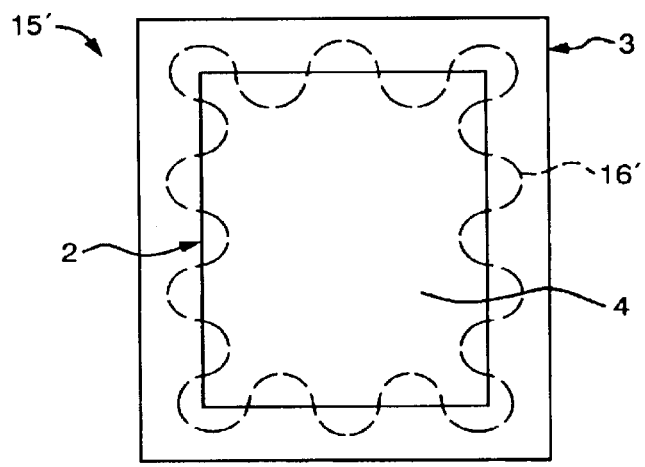

In FIG. 5A, the member 16 is formed in a serpentine pattern. FIG. 5B shows an alternative embodiment similar to that of FIG. 5A, except that the member 16' is configured in an undulating pattern, near the periphery of the pliable pad 15'. As in the embodiment of FIG. 5A, the pliable pad 15' is made formable by the bendable member 16'.

Figure 6:
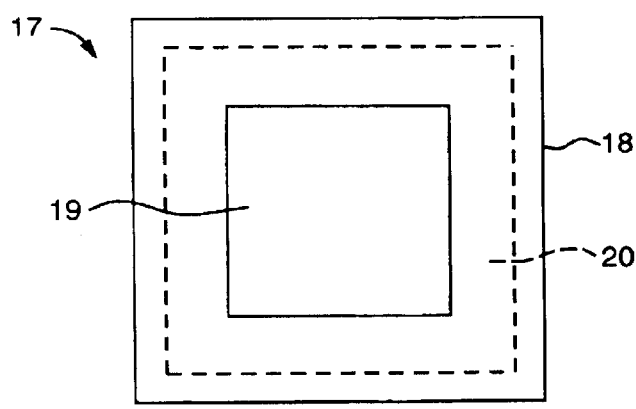
FIG. 6 is a plan view of an alternative embodiment of the pliable pad having a cutout in the formable member, for reducing manufacturing costs.

FIG. 6 shows an alternative embodiment for the pliable pad (17) which includes a formable backing layer 18 comprised of a formable material having a cutout portion 19, the primary purpose of which is to reduce the cost of manufacture. For convenience of illustration, the layer of absorbent material which would ordinarily be combined with the formable backing layer 18 has not been shown in FIG. 6. The formable backing layer 18 preferably includes a liquid barrier layer 20, which can be positioned above (as shown by the dotted outline in FIG. 6) and/or below the formable backing layer 18, as desired for a particular application.

In the embodiment shown in FIG. 6, the cutout portion 19 is generally square or rectangular in shape and is located near the center of the pliable pad. The cutout portion is preferably located at or near the center of the pliable pad because in this region, the strength of the formable material is less critical, primarily because the center portion will normally remain flat, even after the formable material has been shaped to form a basin. Other configurations for the cutout region are equally possible. For example, more than one cutout portion can be provided, and the shape of the cutout portion or portions provided can be varied considerably. Complex patterns can also be developed, if desired for a particular application, such as the combination of a plurality of cutout regions to form a "checkerboard" pattern having squares of material alternating with gaps formed of the plural cutout regions.

Figure 7:
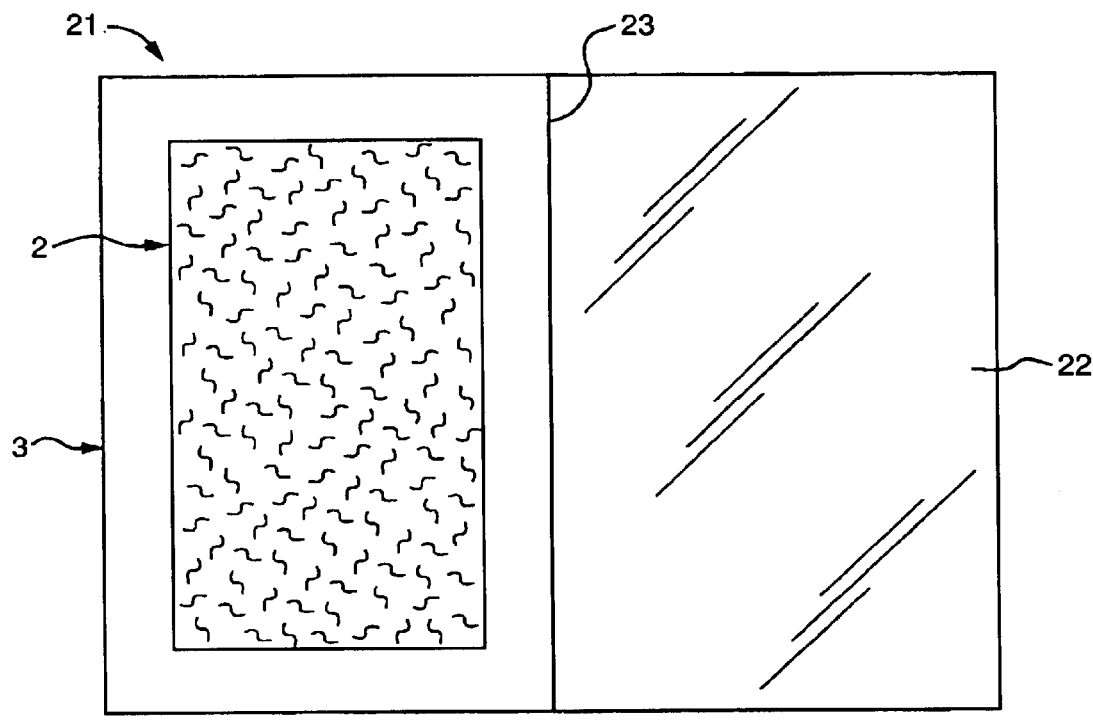
FIG. 7 is a plan view of an alternative embodiment of the pliable pad having a liquid-impervious material which is used as a shield extending from one of its sides.

FIG. 7 shows an alternative embodiment for the pliable pad (21) which includes a spray barrier 22 protruding from a side edge 23 of the pad, in this case extending from a side edge 23 of the backing layer 3. The spray barrier 22 is preferably comprised of a clear sheet of plastic material, but can also be formed of a translucent or opaque material which is substantially impervious to liquids. The spray barrier 22 can either be provided as an extension of one of the liquid barrier layers 9, 9' shown in the embodiments of FIGS. 3A to 3D, or can be separately formed and suitably joined to any of these sheets, or to the layers of formable material 10, 10'. The pliable pad can be provided with plural spray barriers, extending from different structural elements of the pliable pad, if desired.

Figure 8:
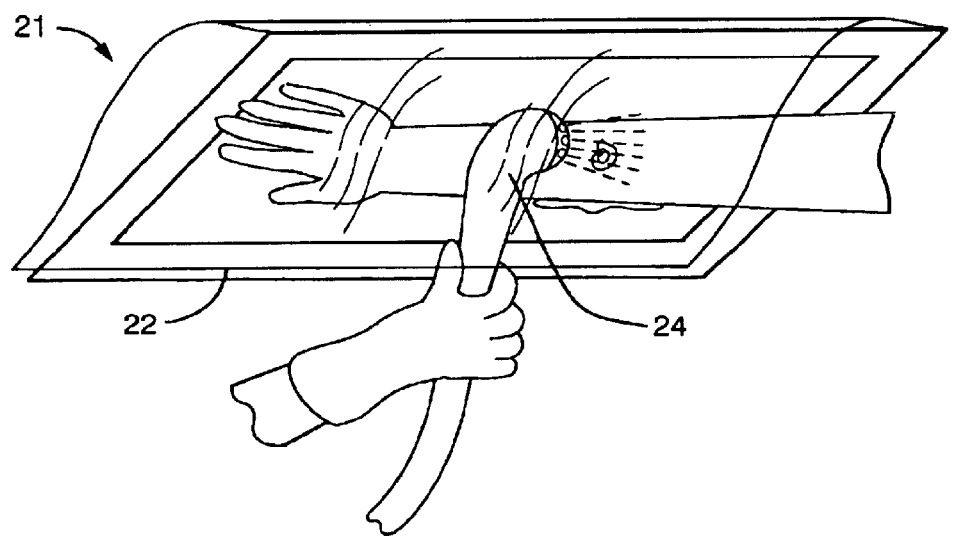
FIG. 8 is an isometric view showing the use of a pliable pad having a plastic shield with a hand-operated spray gun in use underneath the shield.

The spray barrier 22 is used to provide a sheet which can be folded over the patient to form a cover for protecting the user of the pliable pad when spraying fluids within a formed basin. For example, FIG. 8 illustrates use of the pliable pad 21 with a hand-held spray gun 24 which is manipulated underneath the spray barrier 22. The spray barrier 22 prevents liquid issuing from the spray gun 24 from coming into contact with the user.

Figure 9:
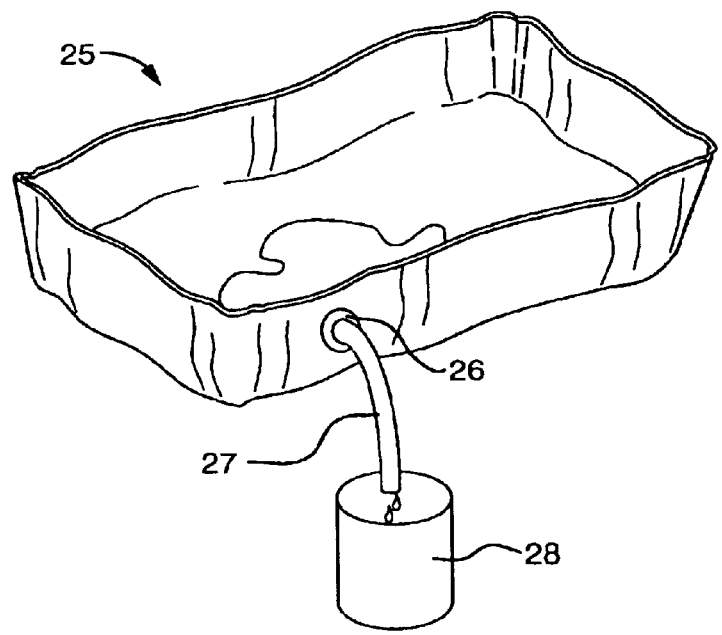
FIG. 9 is an isometric view of an alternative embodiment of the pliable pad which further includes a drain hose connected to a port, to conduct irrigation fluids to a collecting container.

FIG. 9 shows an alternative embodiment for the pliable pad (25), which in this case has already been formed into a basin, and which further includes a drainage port 26. A hose 27 is optionally provided for connection to the drainage port 26, which in this case is implemented as a flange for receiving the hose 27. The port 26 receives fluid collected within the basin formed by the folded pliable pad 25, for conducting the received fluid from the basin to a suitable receptacle, such as the bucket 28. Use of the flanged connection shown in FIG. 9 is preferred so that the drainage port 26 (and any hose it receives) is reliably sealed against the pliable pad 25 to prevent leakage. Multiple drainage ports can also be used, if desired, to provide the pliable pad with plural drains (e.g., along the side or at the bottom of the pad).

Figure 10:
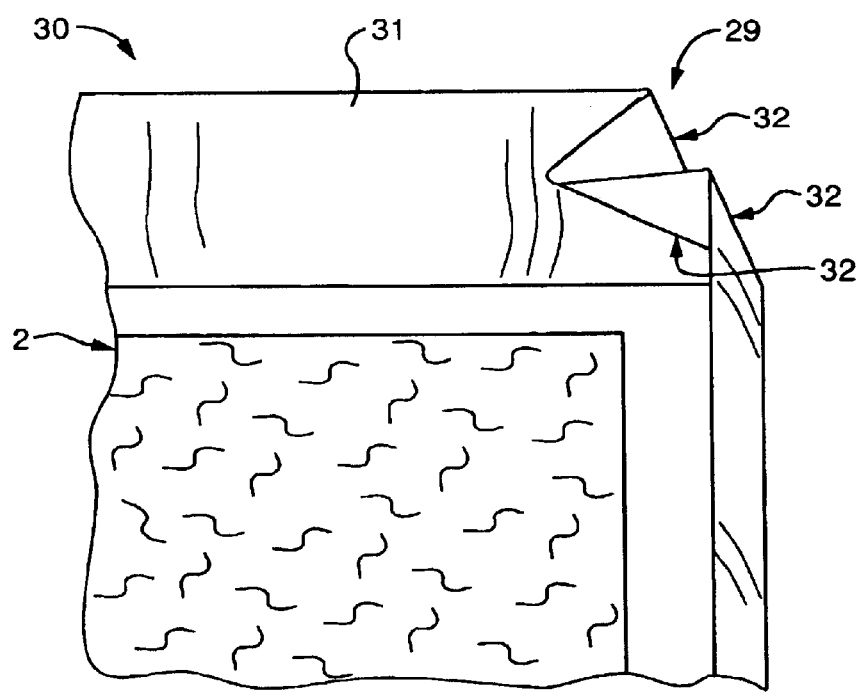
FIG. 10 is a partial, isometric view of a corner of an alternative embodiment of a pliable pad which has been folded to form a basin, in which the formable material includes scoring for assisting in formation of the box-like configuration which is shown.

FIG. 10 shows portions (i.e., the corner 29) of an alternative embodiment for the pliable pad (30) having a layer of formable material 31 which is comprised of paper or stiff cardboard. The paper or stiff cardboard material can then be scored, at 32, so that the resulting backing layer can be more easily shaped (e.g., to form the box-like configuration shown).

Figure 11:
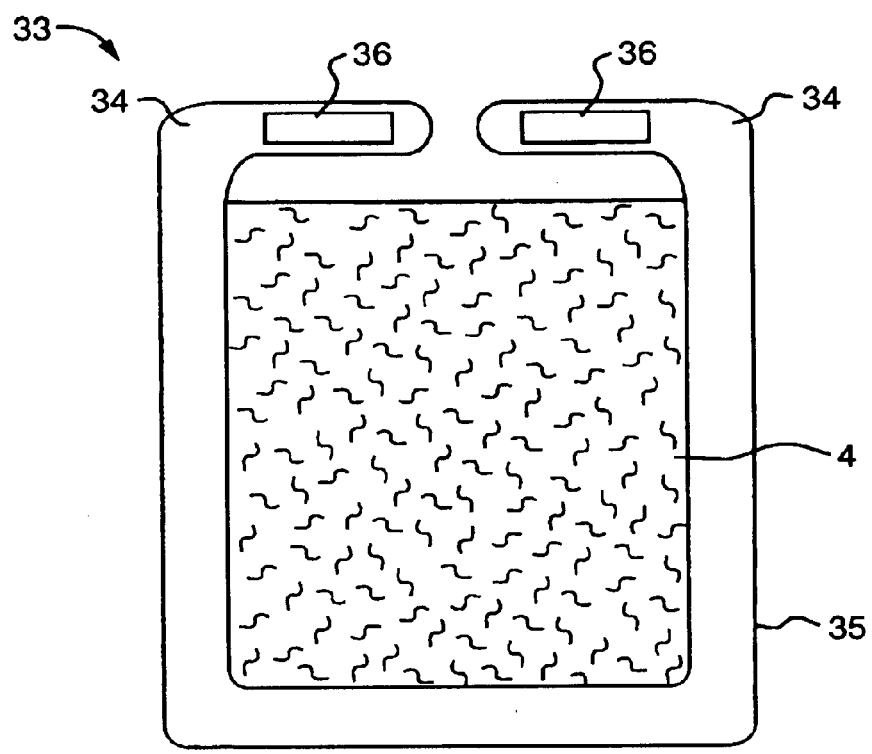
FIG. 11 is a plan view of an alternative embodiment of the pliable pad which includes tabs for securing the pliable pad to a patient or to a desired structure.

FIG. 11 shows an alternative embodiment for the pliable pad (33) which includes a pair of tabs 34 which are formed as extensions of a formable backing layer 35. Such tabs can similarly extend from other portions of the pliable pad, if desired. The tabs 34 are preferably comprised of a plastic material, and can be manufactured to develop any of a variety of different configurations. The configuration shown in FIG. 11 is useful for conserving material, and as a result, reducing the costs of fabrication. It is also possible to form tabs which extend from plural positions on the pliable pad (e.g., from opposing peripheral edges of the formable backing layer), if desired.

Figure 12:
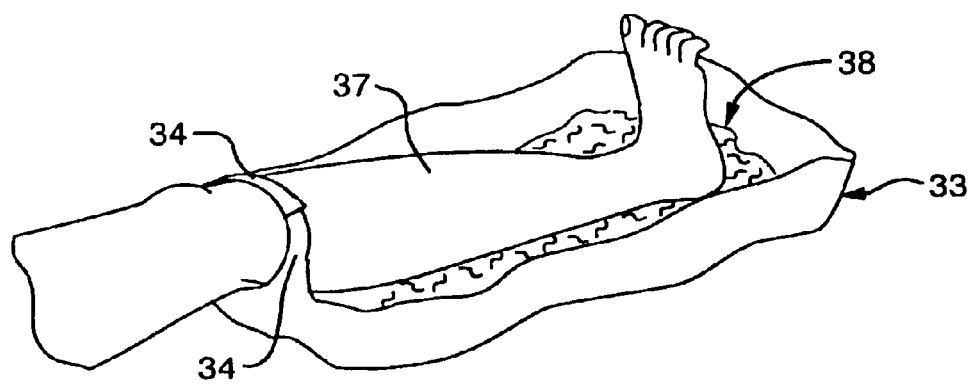
FIG. 12 is an isometric view showing the use of an alternative embodiment of the pliable pad having tabs for securing the pliable pad against a limb.

In use, the tabs 34 can simply be tied together to secure the pliable pad 33 against the limb of a patient. As an alternative, one or more of the tabs 34 can be provided with an adhesive strip 36 for facilitating connection of the tabs 34 to one another. Any of a variety of fasteners can be used to achieve a similar result, such as a hook-and-loop arrangement or some other mechanical fastener, so that the tabs 34 can be conveniently secured to each other. FIG. 12 illustrates the use of tabs 34 having the adhesive strips 36 of FIG. 11 to secure a limb 37 within a defined basin 38. The primary purpose of the tabs 34 is to secure the pliable pad 33 against the patient and create a seal to further prevent the leakage of liquid, and to secure the limb 37 of the patient to the pliable pad 33.

Figure 13:
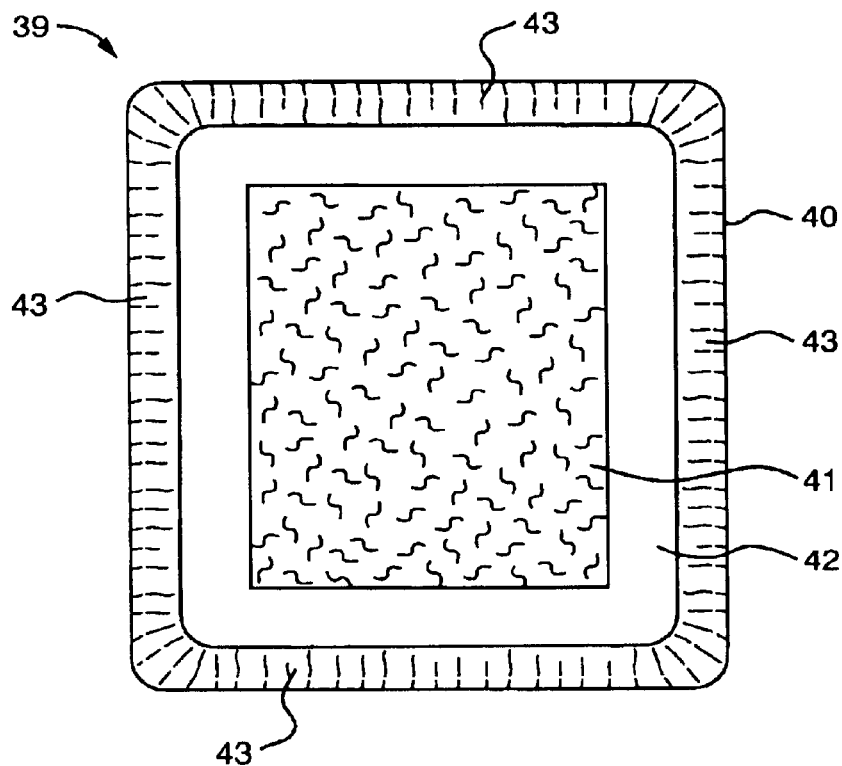
FIG. 13 is a plan view of an alternative embodiment of the pliable pad having a formable foil which is crimped for mechanical attachment to remaining structures of the pliable pad.

FIG. 13 shows an alternative embodiment for the pliable pad (39) which again includes a layer of formable material 40, a layer of absorbent material 41 and a liquid barrier layer 42 (which is optionally provided). In this embodiment, the formable material is a metal foil and the liquid barrier (if used) is a plastic film. The layer of absorbent material 41 is attached to the plastic film forming the liquid barrier layer 42. The edges 43 of the foil which develops the layer of formable material 40 are folded around the corresponding edges of the plastic film which develops the liquid barrier layer 42, if used, or are folded to directly engage the layer of absorbent material 41. Folding the foil layer in this manner eliminates the need to glue or otherwise attach the foil layer 40 to the layer of absorbent material 41, or to the liquid barrier layer 42, if used.

Figure 14:
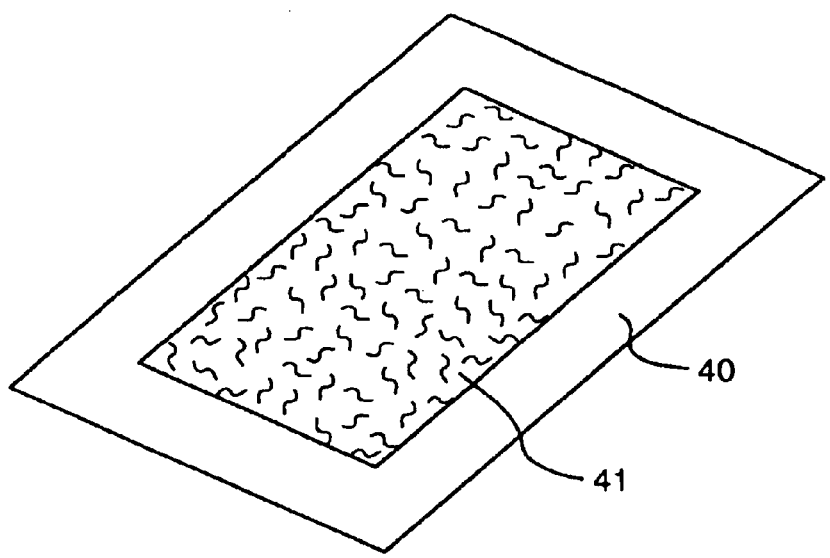
FIGS. 14 to 17 are isometric views illustrating assembly of the embodiment of the pliable pad shown in FIG. 13, during various stages of its manufacture.
Figure 15:
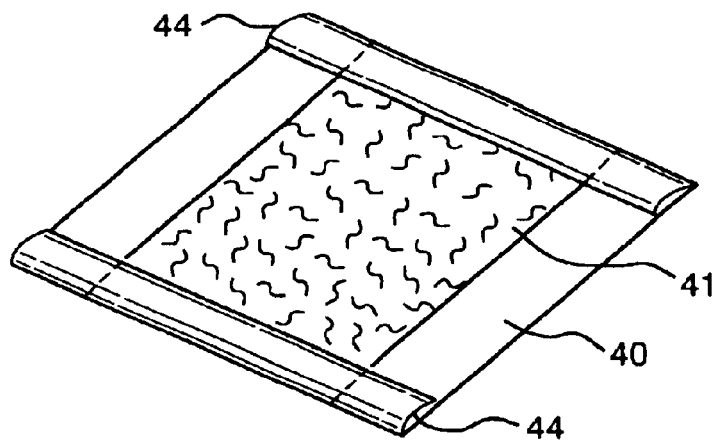
Figure 16:
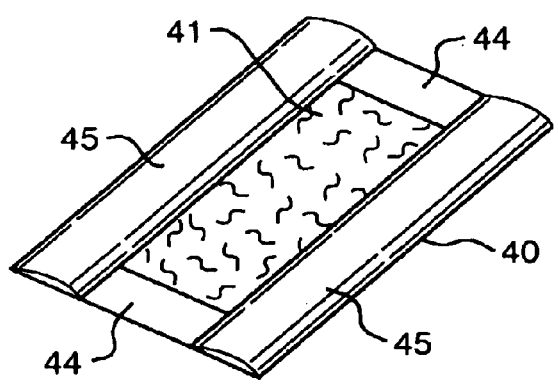
Figure 17:
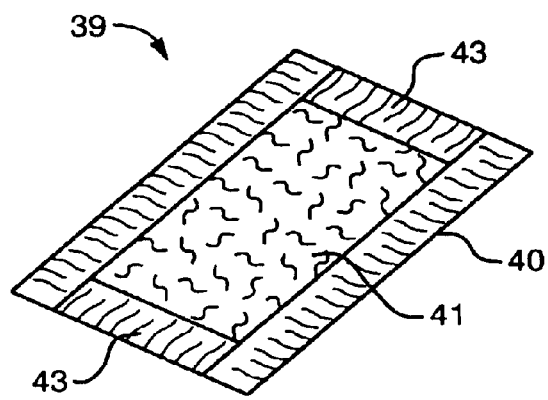

FIGS. 14 to 17 illustrate the various stages of an assembly procedure which can be used to eliminate the need to affix a layer of formable material 40 to other portions of the pliable pad, in this case, a layer of absorbent material 41. In FIG. 14, the layer of absorbent material 41 (with or without a netting, or some other outer layer) is positioned over a backing layer which includes the layer of formable material 40. The layers 40, 41 are not affixed to one another, but are preferably left free of any direct attachment. In this configuration, the backing layer preferably includes one or more layers of plastic sheeting (which serves as a liquid barrier) and a sheet of aluminum or aluminum foil (which serves as the formable material). In FIG. 15, the ends 44 of the layer of formable material 40 have been bent over the layer of absorbent material 41. Following this, the sides 45 of the layer of formable material 40 are bent over, as shown in FIG. 16. The completed (folded) product is shown in FIG. 17. For added strength, the ends and sides of the sheet of formable material 40 can be bent over several times. In any event, the resulting arrangement operates to capture the layer of absorbent material 41 within a frame formed of bent aluminum or aluminum foil, eliminating the need for an adhesive to keep the assembly in place.

Figure 18:
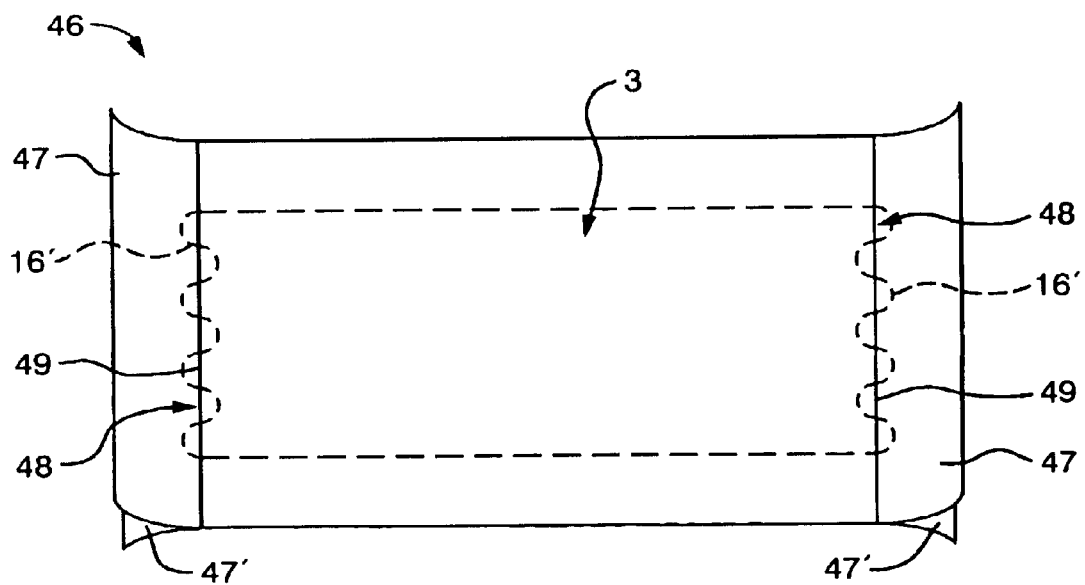
FIG. 18 is an isometric view of an alternative embodiment of the pliable pad having a pair of barrier layers attached to one another, to retain the formable material between the barrier layers.

FIG. 18 shows an alternative embodiment for the pliable pad (46) having a pair of barrier layers 47, 47' which are heat-welded to the formable material (implemented as the member 16' of FIG. 5B). In this configuration, the pair of barrier layers 47, 47' surround the formable member 16', which is shown in phantom because it will then be sandwiched between the pair of barrier layers 47, 47'. The undulating formable material serves to develop serrated edges 48 which, for convenience of illustration, are shown only on two sides. In practice, such serrations can be established on any or all of the sides of the formable material. The barrier layers 47, 47' are heat-welded to each other along the lines 49, which can be continued around the periphery of the formable material, if desired. The welding lines 49 pass through the serrations 48 so that, by heat-welding the barrier layers 47, 47' to each other, the formable member 16' becomes encased within the melted barrier layer material. As a result, the formable member 16' is firmly anchored within and between the pair of barrier layers 47, 47'. This eliminates the need to glue such elements together. A similar result can be achieved for formable materials in sheet form by providing the sheet which serves as the formable material with a series of small holes for alignment with the welding lines 49.

Figure 19:
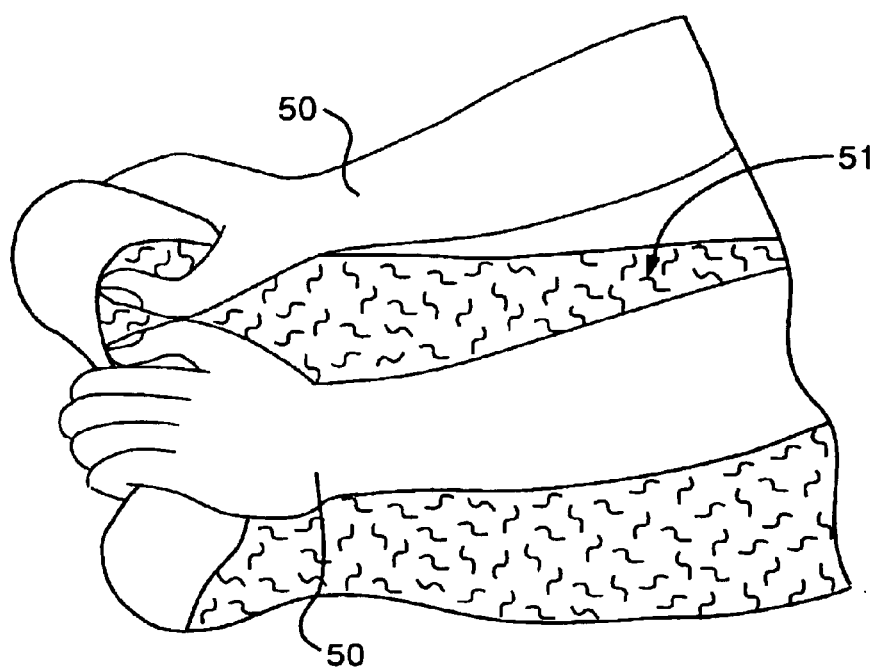
FIG. 19 is a partial, isometric view showing formation of the pliable pad into a basin.
Figure 20:
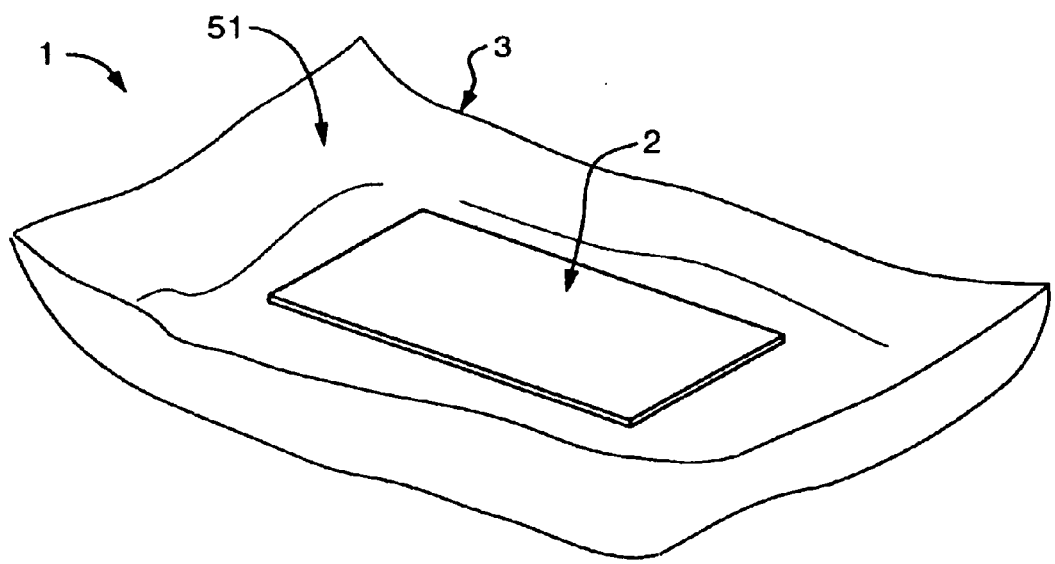
FIG. 20 is an isometric view of the pliable pad after having been formed into a basin.

Prior to use, the pliable pad of the present invention will generally be flat, or substantially so, for convenience of storage. Deployment of the pliable pad will vary, responsive to the desired use for the pliable pad. FIG. 19 illustrates the initial formation of a typical pliable pad, which is being shaped by the hands 50 of a user to form a basin 51. FIG. 20 shows the shaped basin 51, after having been formed.

Figure 21:
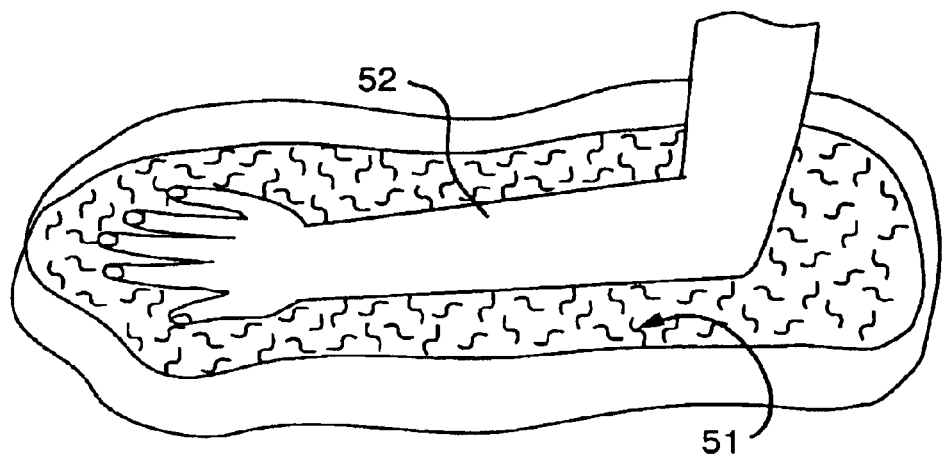
FIG. 21 is a top view showing use of the pliable pad to irrigate a forearm.
Figure 22:
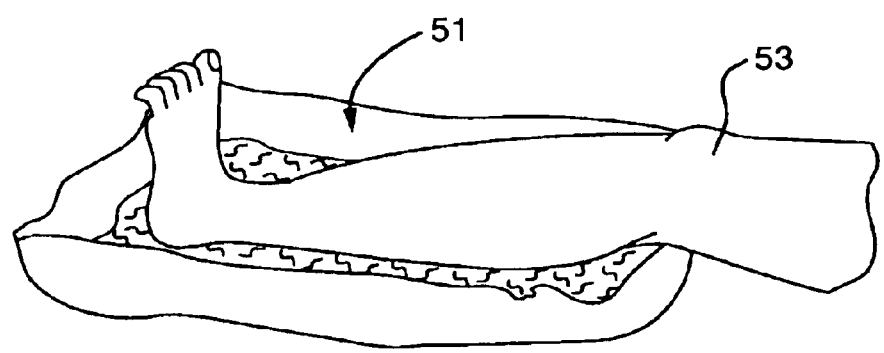
FIG. 22 is an isometric view showing use of the pliable pad to irrigate a leg.
Figure 23:
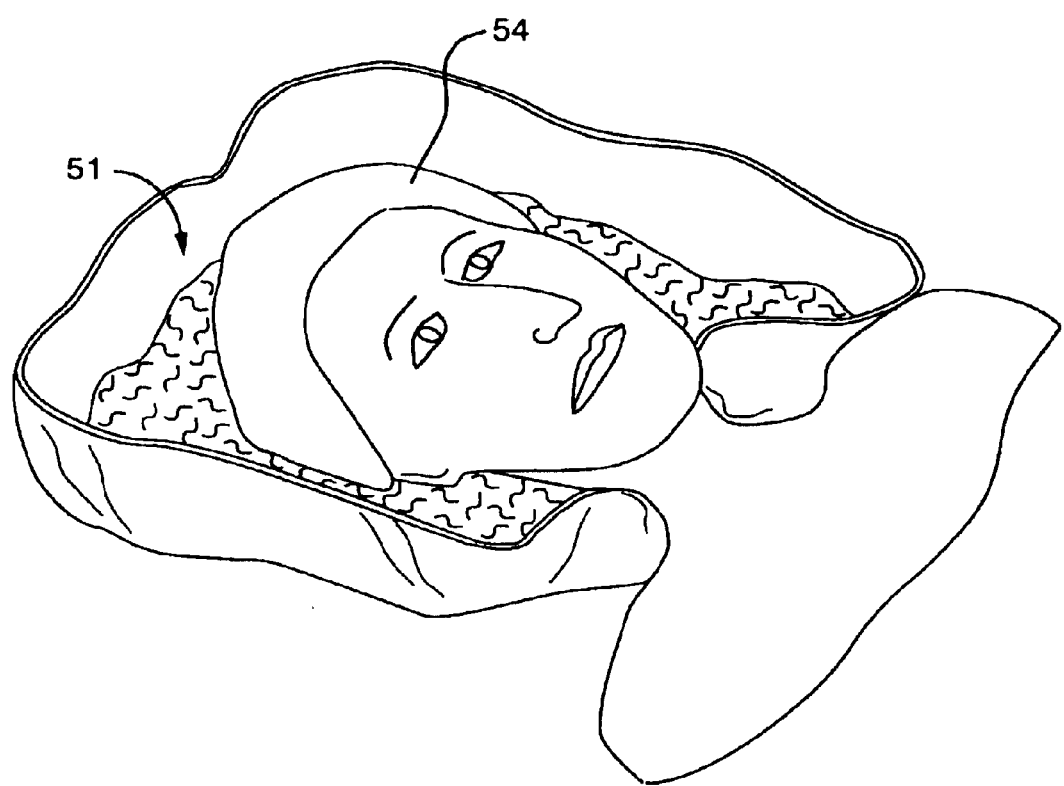
FIG. 23 is a top view showing use of the pliable pad to irrigate portions of a head.

FIG. 21 illustrates use of the pliable pad of the present invention to develop a typical configuration useful for irrigating a forearm 52. To this end, the forearm 52 is placed on the pliable pad, which can either be pre-formed to develop the basin 51 for accommodating the forearm 52, or which can initially be deployed flat (or substantially flat) and then formed around the forearm 52. In either case, the resulting basin 51 which is defined by the pliable pad is made ready to receive water, or some other irrigation fluid. FIG. 22 illustrates a similar configuration for use in irrigating a leg 53. FIG. 23 shows use of the pliable pad for irrigating a patient's head 54 (e.g., to treat an eye or other head wound).

Figure 24:
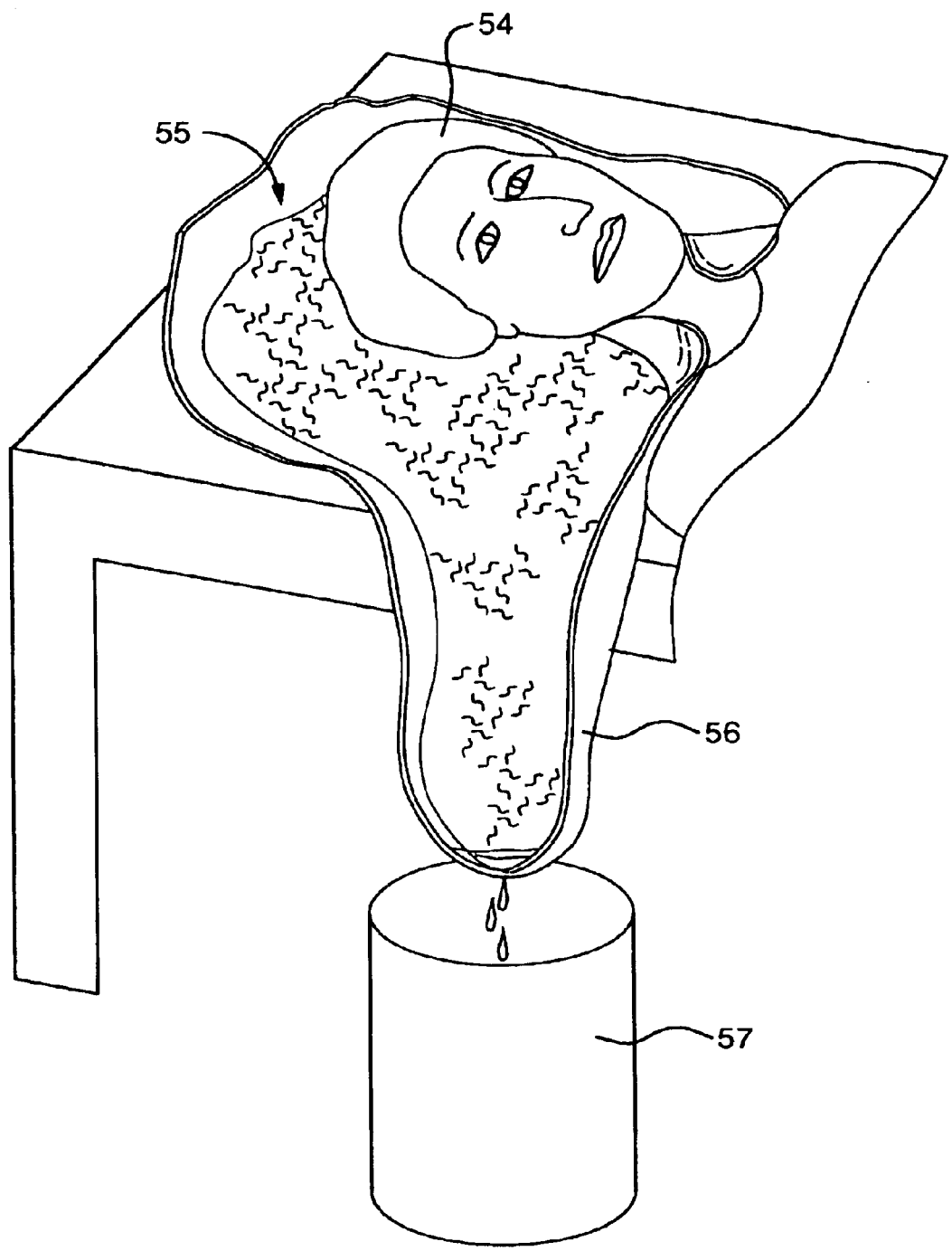
FIG. 24 is an isometric view showing use of the pliable pad to form a drainage channel for directing liquid into a receptacle.

FIG. 24 again shows use of the pliable pad of the present invention, following its formation into a basin 55, to surround the patient's head 54. In this case, portions of the pliable pad have been formed into a drainage channel 56 for directing liquid into a desired receptacle 57. This embodiment provides an alternative to the embodiment shown in FIG. 9, which uses the additional structures of a hose 27 and flange 26 which are not originally part of the pliable pad, to achieve a similar result. In the embodiment of FIG. 24, a portion of the pliable pad itself develops the drain, eliminating the need -to provide additional structures for such purposes.

Figure 25:
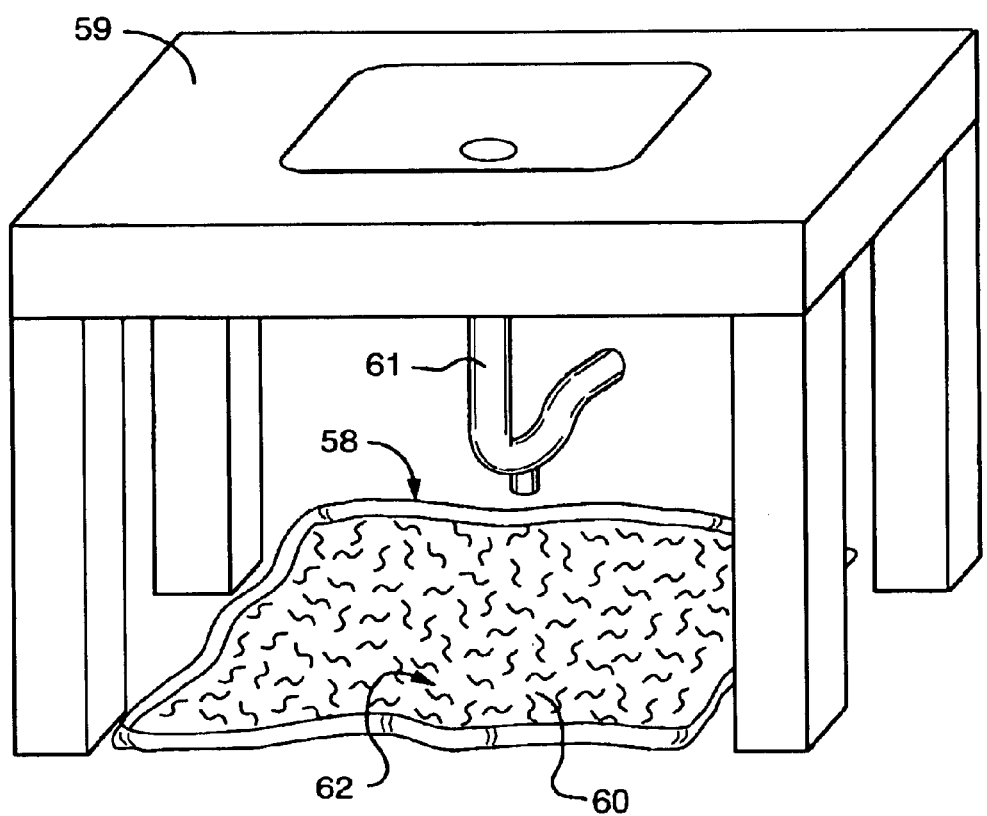
FIG. 25 is an isometric view showing use of the pliable pad in a plumbing application.

The pliable pad of the present invention can also be used to perform a variety of non-medical applications. As an example, FIG. 25 shows use of the pliable pad to develop a fluid-receiving receptacle 58 which can be positioned under a sink 59. The formed receptacle 58 includes a layer of absorbent material 60 which serves to soak up liquid that may leak from the pipes 61. The basin 62 which is defined by the formable material associated with the receptacle 58 serves to contain received liquid, for subsequent collection and removal. A key advantage of this configuration is that the pliable pad can be deployed in a first configuration (e.g., substantially flat or partially folded), to overcome obstacles such as the pipes 61 which would otherwise interfere with the installation of a conventional basin, and then assume a second configuration which is best suited to capture leaking fluid (e.g., a basin formed by desired shaping of the pliable pad, or by shaping the pliable pad to surround the leak). The pliable pad of the present invention similarly can be used to accommodate fluids associated with machinery (e.g., coolants, lubricants, and the like).

It will therefore be understood that various changes in the details, materials and arrangement of parts which have been herein described and illustrated in order to explain the nature of this invention may be made by those skilled in the art within the principle and scope of the invention as expressed in the following claims.

What is claimed is:

1. An apparatus for collecting and absorbing spilled liquid, comprising:
 a layer formed of an absorbent material, wherein the absorbent material is capable of absorbing the liquid; and
 a formable material coupled with the layer formed of the absorbent material, wherein the formable material is formed of a bendable material which is capable of retaining a shape assumed by the formable material after shaping, wherein the formable material has a generally planar configuration before shaping, and wherein at least portions of the layer formed of the absorbent material cover at least portions of the formable material.

2. The apparatus of claim 1 wherein the absorbent material is selected from the group of absorbent materials consisting essentially of superabsorbent polymers, absorbent gauze and pulp materials.

3. The apparatus of claim 1 wherein the layer of the absorbent material has a thickness in a range of from about ⅛ to about ¼ inches.

4. The apparatus of claim 1 wherein the layer of the absorbent material has a thickness in a range of from about 1 to about 2 inches.

5. The apparatus of claim 1 which further includes a support mated with the apparatus to raise an object placed on the apparatus.

6. The apparatus of claim 5 wherein the support is positioned over the layer formed of the absorbent material.

7. The apparatus of claim 5 wherein the support is positioned beneath the layer formed of the absorbent material.

8. The apparatus of claim 1 wherein the layer formed of the absorbent material has lateral edges and a defined area, wherein the formable material has a defined area, and wherein the area of the formable material is greater than the area of the absorbent material so that the formable material extends beyond the edges of the layer formed of the absorbent material.

9. The apparatus of claim 1 wherein the layer formed of the absorbent material has lateral edges and a defined area, wherein the formable material has a defined area, and wherein the area of the formable material is approximately equal to the area of the absorbent material so that the formable material is substantially coextensive with the edges of the layer formed of the absorbent material.

10. The apparatus of claim 1 wherein the layer formed of the absorbent material has lateral edges and a defined area, wherein the formable material has a defined area, and wherein the area of the absorbent material is greater than the area of the formable material so that the edges of the layer formed of the absorbent material extend beyond the formable material.

11. The apparatus of claim 1 wherein the layer formed of the absorbent material has a defined area including a center, wherein the formable material has a defined area including a center, and wherein the center for the layer formed of the absorbent material substantially corresponds with the center for the formable material.

12. The apparatus of claim 1 wherein the formable material is selected from the group of shape-retaining members consisting essentially of thin aluminum sheets, aluminum foils, metal wires, metal rods and metal bands.

13. The apparatus of claim 1 wherein the formable material is attached to the layer formed of the absorbent material.

14. The apparatus of claim 13 wherein the formable material includes edges which are bent over the layer formed of the absorbent material to mechanically attach the formable material and the layer formed of the absorbent material.

15. The apparatus of claim 1 wherein the formable material is crinkled.

16. The apparatus of claim 1 which further includes a liquid barrier material coupled with the layer formed of the absorbent material and the formable material.

17. The apparatus of claim 16 wherein the liquid barrier material is a sheet, a film or a coating selected from the group of liquid-impervious materials consisting essentially of vinyl, polyethylene and polypropylene.

18. The apparatus of claim 16 wherein the liquid barrier material is a plurality of layers formed of the liquid barrier material.

19. The apparatus of claim 18 which further includes a support positioned between the plural layers formed of the liquid barrier material, to raise an object placed on the apparatus.

20. The apparatus of claim 19 wherein the layer formed of the absorbent material is comprised of plural members formed of the absorbent material and positioned adjacent to the support.

21. The apparatus of claim 16 wherein a layer formed of the liquid barrier material is coupled with the layer formed of the absorbent material.

22. The apparatus of claim 16 wherein a layer formed of the liquid barrier material is coupled with the formable material.

23. The apparatus of claim 16 wherein the liquid barrier material is a sheet disposed beneath the layer formed of the absorbent material.

24. The apparatus of claim 23 wherein the layer formed of the absorbent material is attached to the sheet forming the liquid barrier material.

25. The apparatus of claim 1 having plural layers of the formable material.

26. The apparatus of claim 25 wherein at least one layer of a liquid barrier material is positioned between the plural layers of the formable material.

27. The apparatus of claim 1 wherein the formable material is enclosed by at least one sheet of material.

28. The apparatus of claim 27 wherein the at least one sheet of material which encloses the formable material is formed of a liquid barrier material.

29. The apparatus of claim 28 wherein the formable material defines at least one serrated edge, and wherein plural sheets of the liquid barrier material are attached to each other along a seam which engages the serrated edge.

30. The apparatus of claim 29 wherein the plural sheets of the liquid barrier material are heat welded to each other along the serrated edge.

31. The apparatus of claim 29 wherein the formable material is non-adhesively secured between the plural sheets of the liquid barrier material.

32. The apparatus of claim 1 wherein the layer formed of the absorbent material is enclosed within an outer layer which retains the absorbent material within a confined space and which allows fluid to pass through the outer layer to the layer formed of the absorbent material.

33. The apparatus of claim 32 wherein the layer formed of the absorbent material has a top surface which is disposed adjacent to the outer layer, and wherein a layer formed of a liquid impervious material is positioned along the top surface of the layer formed of the absorbent material.

34. The apparatus of claim 33 wherein the layer formed of the liquid impervious material does not fully enclose the layer formed of the absorbent material.

35. The apparatus of claim 33 wherein the layer formed of the liquid impervious material is only provided on the top surface of the layer formed of the absorbent material.

36. The apparatus of claim 32 wherein at least portions of the outer layer are formed of a mesh-like material.

37. The apparatus of claim 36 wherein top portions of the outer layer are formed of a liquid impervious material and sides of the outer layer are formed of the mesh-like material.

38. The apparatus of claim 32 wherein the outer layer completely encloses the layer formed of the absorbent material.

39. The apparatus of claim 32 wherein the outer layer is attached to the formable material.

40. The apparatus of claim 32 wherein the outer layer is attached to a liquid barrier material associated with the formable material.

41. The apparatus of claim 1 which further includes a sheet formed of a liquid-impervious material which can be folded over the layer formed of the absorbent material to define a spray barrier.

42. The apparatus of claim 41 wherein the sheet formed of the liquid-impervious material extends from the formable material.

43. The apparatus of claim 41 wherein the sheet formed of the liquid-impervious material is integral with a layer formed of a liquid barrier material which is coupled with the layer formed of the absorbent material and the formable material.

44. The apparatus of claim 1 which further includes at least one tab for securing the apparatus around an object.

45. The apparatus of claim 44 having at least two tabs, and means associated with at least one of the tabs for connecting the tabs together to secure the apparatus to the object.

46. The apparatus of claim 1 wherein the formable material includes a cutout portion.

47. The apparatus of claim 46 wherein the cutout portion is positioned along central portions of the apparatus.

48. The apparatus of claim 46 wherein the formable material includes a plurality of cutout portions.

49. The apparatus of claim 1 which further includes a drain formed in portions of the apparatus.

50. The apparatus of claim 49 wherein the drain is connected to an external hose for conveying liquid away from a basin formed with the apparatus.

51. The apparatus of claim 1 wherein portions of the formable material are shaped to form a drainage channel.

52. The apparatus of claim 1 wherein portions of the formable material are scored, and wherein the scored portions define a corner for a folded side wall developed with the formable material.

53. The apparatus of claim 1 wherein the formable material is an elongate member which is bendable, and which retains an assumed shape after bending.

54. The apparatus of claim 53 wherein the elongate member has a serpentine configuration which extends across central portions of the apparatus.

55. The apparatus of claim 53 wherein the elongate member has an undulating configuration which extends around peripheral portions of the apparatus.

56. The apparatus of claim 53 wherein the elongate member is a solid rod.

57. The apparatus of claim 53 wherein the elongate member is a hollow tube.

58. The apparatus of claim 1 which is pre-folded to assume a substantially flat configuration which is easily opened and made ready for use.

59. The apparatus of claim 1 wherein the absorbent material initially has a generally planar configuration.

\* \* \* \* \*